United States Patent [19]

Numata et al.

[11] 4,238,608
[45] Dec. 9, 1980

[54] 7-[2-(2-AMINOTHIAZOL-4-YL)-2-SUBSTITUTED THIO-ACETAMIDO] CEPHALOSPORINS

[75] Inventors: Mitsuo Numata; Masayoshi Yamaoka, both of Osaka, Japan

[73] Assignee: Takeda Chemical Industries, Ltd., Japan

[21] Appl. No.: 43,323

[22] Filed: May 29, 1979

[30] Foreign Application Priority Data

Jun. 2, 1978 [JP] Japan .................. 53/67006

[51] Int. Cl.³ .................. C07D 501/34; C07D 501/46; C07D 501/56; A61K 31/545
[52] U.S. Cl. .................. 544/027; 544/22; 544/25; 544/28; 424/246
[58] Field of Search .................. 544/25, 27, 28, 22; 424/246

[56] References Cited
U.S. PATENT DOCUMENTS

| | | | |
|---|---|---|---|
| 4,080,498 | 3/1978 | Numata et al. | 544/27 |
| 4,098,888 | 7/1978 | Ochiai et al. | 424/246 |
| 4,132,789 | 1/1979 | Nomura et al. | 424/246 |
| 4,137,406 | 1/1979 | Tsuchihashi et al. | 544/27 |

*Primary Examiner*—Donald G. Daus
*Assistant Examiner*—Diana G. Rivers
*Attorney, Agent, or Firm*—Craig & Antonelli

[57] ABSTRACT

A novel compound of the formula:

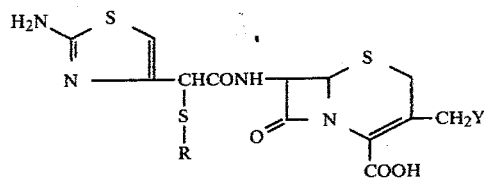

wherein R is lower alkyl or a group of the formula

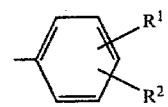

where $R^1$ and $R^2$ are the same or different and each is hydrogen, carboxyl or halogen; Y is acyloxy or a group of the formula —S—Het where Het is a nitrogen-containing heterocyclic group which may optionally be substituted, or a pharmaceutically acceptable salt thereof is found to be effective for treatment of diseases in animals including domestic fowls and human beings, particularly the infectious diseases caused by gram-positive and gram-negative bacteria.

19 Claims, No Drawings

7-[2-(2-AMINOTHIAZOL-4-YL)-2-SUBSTITUTED THIO-ACETAMIDO] CEPHALOSPORINS

This invention relates to cephalosporin derivatives or salts thereof which are novel antimicrobial agents of value for the treatment of diseases in animals including domestic fowls and human beings, particularly the infectious diseases caused by gram-positive and gram-negative bacteria, which cephalosporin derivatives have a novel 7-acyl group and are represented by the general formula:

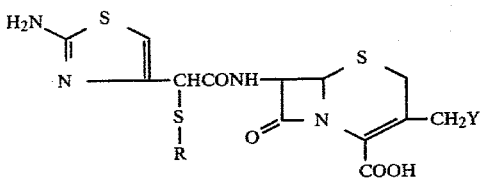

[wherein R is lower alkyl or a group of the formula

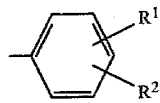

($R^1$ and $R^2$ are the same or different and each is hydrogen, carboxyl or halogen); Y is acyloxy or a group of the formula —S—Het (Het is a nitrogen-containing heterocyclic group which may optionally be substituted)]. In another aspect, this invention relates to a method of producing such cephalosporin derivatives.

Currently on the market are several semi-synthetic cephalosporins known to possess broad antimicrobial spectra, and these cephalosporins have been used clinically for the treatment of various infectious diseases. There are, however, not a few clinically significant bacteria which are resistant to those known drugs. For example, certain species of Escherichia coli, certain species of pathogenic bacteria of the genus Citrobacter, the majority of indolepositive bacteria of the genus Proteus and pathogenic bacteria belonging to the genera of Enterobacteria, Serratia, Pseudomonas, etc. are resistant to the known cephalosporins [cf. w. E. Wick, "Cephalosporins and Penicillins; Chemistry and Biology", E. H. Flynn, Ed., Academic Press, New York, N.Y., 1972, Chapter II.]. Therefore, a search is still underway for new cephalosporins which will be clinically active against the aforementioned pathogenic microorganisms.

After an intensive research the present inventors have found that a compound of the following general formula [II] or a salt thereof, when reacted with thiourea, gives rise to a new 7-[2-(2-aminothiazol-4-yl)-2-substituted thio-acetamido]cephalosporin derivative of the formula [I] or a salt thereof and that this new cephalosporin derivative [I] or a salt thereof is very desirable in that it is highly anti-bacterial to various bacteria including the gram-negative bacteria resistant to the aforementioned known cephalosporin drugs.

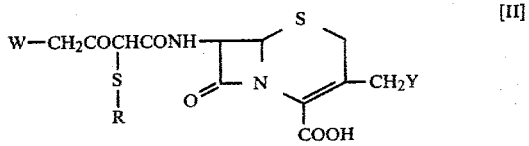

[wherein W is halogen; R and Y have the meanings respectively defined hereinbefore]

Thus, the cephalosporin derivative [I] or a salt thereof is a new antibiotic agent which displays high antibacterial activity against a broad spectrum of gram-negative bacteria such as Escherichia coli, Klebsiella pneumoniae, Proteus vulgaris, Proteus mirabilis, Proteus morganii, Proteus rettgeri, Citrobacter freundii, Enterobacter cloacae and Serratia marscecens, and is of value for the treatment and prophylaxis of the various diseases caused by such bacteria in mammalian animals including domestic fowls and human beings.

Referring, now, to the above formulas, the lower alkyl represented by the symbol R means a straight-chain or branched lower alkyl group of not more than 3 carbon atoms (e.g. methyl, ethyl, n-propyl, isopropyl), although methyl is particularly desirable. The symbol R also means a group of the formula

($R^1$ and $R^2$ are the same or different and each is hydrogen, carboxyl or halogen). The halogen $R^1$ or/and $R^2$ means chlorine, bromine, iodine or fluorine. Preferably, $R^1$ is carboxyl and $R^2$ hydrogen, chlorine or bromine. The acyloxy represented by the symbol Y may for example be an alkylcarbonyloxy group of 2 to 4 carbon atoms, e.g. acetyloxy or propionyloxy; a phenylacetyloxy group which may optionally be substituted by hydroxyl, sulfo, amino or other group in the α-position, e.g. mandeloxy, α-sulfophenylacetyloxy, glycyloxy or phenylacetyloxy; a carboxysubstituted alkylcarbonyloxy group of 2 to 4 carbon atoms, e.g. succinoyloxy; a group of the general formula:

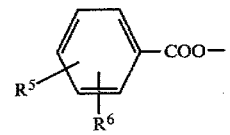

[wherein $R^5$ and $R^6$ each is hydrogen, carboxyl, carbethoxycarbamoyl, carbethoxysulfamoyl or nitro], e.g. 2-carboxybenzoyloxy, 2-(carbethoxycarbamoyl)-benzoyloxy, 2-(2-carbethoxysulfamoyl)benzoyloxy, 2-carboxy-3 (or 4 or 6)-nitrobenzoyloxy or 2,4-dicarboxybenzoyloxy; acetoacetoxy; or carbamoyloxy, although an alkylcarbonyloxy group of 2 to 4 carbon atoms, such as acetoxy or propionyloxy, is preferred. Particularly desirable is acetoxy. The nitrogen-containing heterocyclic group represented by Het in —S—Het is a nitrogen-containing heterocyclic group including at least one nitrogen atom which may be in the oxide form, which heterocyclic group may further include such hetero atoms as oxygen or/and sulfur in addition to nitrogen and be nuclearly substituted. As such a nitrogen-containing heterocyclic group there may be frequently used pyridyl, N-oxopyridyl, pyrimidyl, pyridazinyl, N-oxopyridazinyl, pyrazolyl, diazolyl, thiazolyl, 1,2,3-thiadiazolyl, 1,2,4-thiadiazolyl, 1,3,4-thiadiazolyl, 1,2,5-thiadiazolyl, oxazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, etc. As the substituent or substituents optionally present on such a nitrogen-containing heterocyclic group there may be used a monovalent group, for example, lower alkyl groups ($C_{1-4}$) such as methyl, ethyl, propyl, isopropyl, butyl, isobutyl, etc.; trifluoromethyl; lower alkoxyl groups ($C_{1-4}$) such as methoxy, ethoxy, propoxy, isopropoxy, butoxy, etc.; halogens such as chlorine, bromine, etc.; hydroxyl; mercapto; amino; carboxyl; carbamoyl; etc.; or groups represented by the formulas —$(CH_2)_n$—$Q^1$, —S—$Q^2$,

etc. wherein n is an integer of 1 to 3, $Q^1$ may for example be hydroxyl, mercapto, amino, guanyl, morpholino, carboxyl, sulfo, carbamoyl, alkoxy ($C_{1-4}$) carbonyl, lower alkyl($C_{1-4}$)carbamoyl, alkoxy($C_{1-4}$), alkyl ($C_{1-4}$)thio, alkyl($C_{1-4}$)sulfonyl, acyl($C_{1-4}$)oxy or morpholinocarbonyl, $Q^2$, $Q^3$ and $Q^4$ may for example be a lower alkyl group or a group of the formula —$(CH_2)_n$—$Q^1$, or $Q^3$ and $Q^4$ may also for example be carboxyl, alkoxy ($C_{1-4}$)carbonyl, acyl($C_{1-4}$), carbamoyl or lower alkyl($C_{1-4}$) carbamoyl.

Thus, as practical embodiments, there may be mentioned the groups represented by the formula —$(CH_2)_n$—$Q^1$ such as carboxymethyl, carbamoylmethyl, N-lower alkylcarbamoylmethyl (e.g. N,N-dimethylcarbamoylmethyl), hydroxy-lower alkyl (e.g. hydroxymethyl, 2-hydroxyethyl), acyloxy-lower alkyl (e.g. acetoxymethyl, 2-acetoxyethyl), alkoxycarbonylmethyl (e.g. methoxycarbonylmethyl, hexyloxycarbonylmethyl, octyloxycarbonylmethyl), methylthiomethyl, methylsulfonylmethyl, N-lower alkylamino-lower alkyl (e.g. N,N-dimethylaminomethyl, N,N-dimethylaminoethyl, N,N,N-trimethylammoniumethyl), morpholinomethyl, guanylmethyl, guanylethyl, etc.; the groups represented by the formula

such as lower alkylamino (e.g. methylamino), sulfolower alkylamino (e.g. 2-sulfoethylamino), hydroxy-lower alkylamino (e.g. hydroxyethylamino), lower alkylamino-lower alkylamino (e.g. 2-dimethylaminoethylamino, 2-trimethylammoniumethylamino), acylamino (e.g. acetylamino), 2-dimethylaminoacetylamino, 2-trimethylammoniumacetylamino, lower alkoxycarbonylamino (e.g. methoxycarbonylamino), etc.; and the groups represented by the formula —S—$Q^2$ such as methylthio, 2-hydroxyethylthio, 2-acyloxyethylthio (e.g. 2-acetoxyethylthio, 2-phenylacetoxyethylthio, 2-caproyloxyethylthio), carboxymethylthio, alkoxycarbonylmethylthio (e.g. methoxycarbonylmethylthio, hexyloxycarbonylmethylthio), carbamoylmethylthio, N-lower alkylcarbamoylmethylthio (e.g. N,N-dimethylcarbamoylmethylthio), acetylmethylthio, N-lower alkylamino-lower alkylthio (e.g. 2-N,N-dimethylamino-ethylthio, 2-N,N,N-trimethylammoniumethylthio), morpholinocarbonylmethylthio, 2-sulfoethylthio, etc.

The —S—Het group is preferably a group of the formula

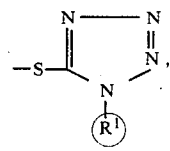

the formula

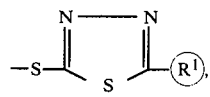

the formula

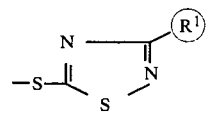

or the formula

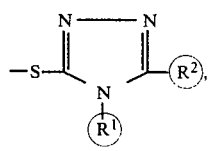

where $R^1$ is hydrogen, a lower alkyl group of 1 to 3 carbon atoms (e.g. methyl), a hydroxy-substituted lower ($C_{1-3}$) alkyl group (e.g. 2-hydroxyethyl), a carboxy lower ($C_{1-3}$) alkyl group (e.g. carboxymethyl), or a di-lower ($C_{1-3}$) alkyl amino lower ($C_{1-3}$) alkyl group (e.g. 2-di-methylaminoethyl); $R^2$ is a lower ($C_{1-3}$) alkyl group (e.g. methyl) or a hydroxy-substituted lower ($C_{1-3}$) alkyl group (e.g. hydroxymethyl).

The objective compound [I] of the present invention has an asymmetric carbon substituted with the group —S—R and hence may be obtained as d-isomer, l-isomer or a mixture thereof.

Among compounds of the above formula [I], particularly desirable compounds are 7-[2-(2-aminothiazol-4-yl)-2-substituted thioacetamido]cephalosporin compounds of the following formula:

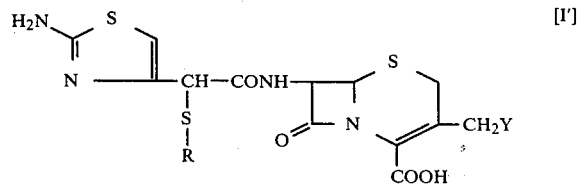

[wherein R is methyl; and Y is acetoxy, carbamoyloxy or a group of the formula the formula

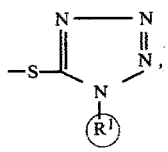

the formula

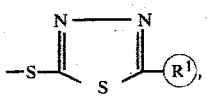

the formula

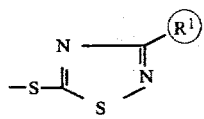

or the formula

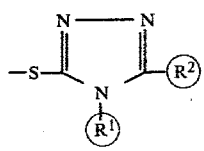

(where $R^1$ is hydrogen, methyl, 2-hydroxyethyl, carboxymethyl or 2-dimethylaminoethyl; and $R^2$ is hydrogen or methyl.)].

The compounds [I] or salts thereof wherein R is represented by the

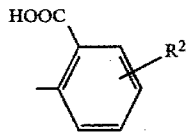

(where $R^2$ is the same as defined above) exhibit excellent activity especially against *Pseudomonas aeruginosa*.

As a drug for the treatment of infectious diseases, the compound [I] is employed in the free form, as a zwitter ion or as a pharmacologically acceptable nontoxic salt which also falls within the scope of compounds of this invention. As such salts of compound [I], there may be mentioned, among others, the corresponding alkali metal salts (e.g. sodium and potassium salts), alkaline earth metal salts (e.g. calcium and magnesium salts), salts with inorganic bases (e.g. ammonium salt), salts with organic bases (e.g. trimethylamine, triethylamine, pyridine, N-methylglucamine, diethanolamine and triethanolamine salts), salts with organic acids (e.g. acetate, tartarate and methanesulfonate), salts with inorganic acids (e.g. hydrochloride, hydrobromide, sulfate and phosphate) and salts with amino acids (e.g. arginine salt, aspartate and glutamate.)

To employ the compound [I] of this invention in the treatment of an infectious diseases, it can be safely administered in the same manner as the known cephalosporins, as formulated in the routine manner with a physiologically acceptable carrier or excipient, i.e. in such dosage forms as solutions and suspensions. Further, the compound [I] is used as a safe drug for the treatment of inflammatory diseases, purulent diseases, respiratory organ infections, bile duct infections, intestinal infections, urinary tract infections and gyneco-obstetric infections in man as caused by the aforementioned bacteria. For example, the following of the compounds [I] of this invention are preferably administered by the intramuscular or intravenous route at the daily adult dose level of about 1 to 100 mg per kilogram body weight and for still better results, 10 to 20 mg on the same basis, in a single dose or 2 to 4 equal portions daily.

(1) Sodium 7-[2-(2-aminothiazol-4-yl)-2-methylthioacetamido]-3-(1-methyl-1H-tetrazol-5-yl)thiomethyl-3-cephem-4-carboxylate;

(2) Disodium 7-[2-(2-aminothiazol-4-yl)-2-(2-carboxyphenylthio)acetamido]-3-(1-methyl-1H-tetrazol-5-yl)thiomethyl-3-cephem-4-carboxylate;

(3) 7-[2-(2-aminothiazol-4-yl)-2-(2-carboxyphenylthio)-acetamido]-3-[1-(2-dimethylaminoethyl)-1H-tetrazol-5-yl]-thiomethyl-3-cephem-4-carboxylic acid;

(4) Disodium 7-[2-(2-aminothiazol-4-yl)-2-(2-carboxyphenylthio)acetamido]-3-(1,3,4-thiadiazol-5-yl)thiomethyl-3-cephem-4-carboxylate;

(5) Disodium 7-[2-(2-aminothiazol-4-yl)-2-(2-carboxyphenylthio)acetamido]-3-(2-methyl-1,3,4-thiadiazol-5-yl)-thiomethyl-3-cephem-4-carboxylate;

(6) Disodium 7-[2-(2-aminothiazol-4-yl)-2-(2-carboxyphenylthio)acetamido]-3-acetoxymethyl-3-cephem-4-carboxylate;

(7) Disodium 7-[2-(2-aminothiazol-4-yl)-2-(2-carboxyphenylthio)acetamido]-3-[1-(2-hydroxyethyl)-1H-tetrazol-5-yl]thiomethyl-3-cephem-4-carboxylate;

(8) Disodium 7-[2-(2-aminothiazol-4-yl)-2-(2-carboxyphenylthio)acetamido]-3-carbamoyloxymethyl-3-cephem-4-carboxylate; and (9) Disodium 7-[2-(2-aminothiazol-4-yl)-2-(2-carboxy-5-chlorophenylthio)acetamido]-3-(1-methyl-1H-tetrazol-5-yl)thiomethyl-3-cephem-4-carboxylate.

The compound [I] according to this invention is a novel compound which can be produced, for example by the following methods.

METHOD 1

The contemplated compound [I] or a salt thereof of this invention can be produced by reacting a compound of formula [II] or a salt thereof with thiourea.

This reaction is generally carried out by reacting each mole of compound [II] or a salt thereof (as mentioned in connection with the compound [I]) with 1 to 4 moles of thiourea.

Normally this reaction is preferably carried out in a solvent, such as dimethylformamide, dimethylacetamide, dioxane, tetrahydrofuran, ethyl acetate, acetone, hexamethylphosphortriamide, dichloromethane or chloroform or an appropriate mixture of such solvents. The reaction of [II] or a salt thereof with thiourea may be carried out at 0°–80° C. and preferably at 0° to 25° C.

The reaction time may generally be 0.5 to 15 hours and satisfactory results may normally be obtained after 1 to 3 hours.

The resulting compound [I] or a salt thereof can be isolated and purified by procedures known per se, e.g. by solvent extraction, pH adjustment, phasic transfer, crystallization, recrystallization, chromatography, etc.

The compound [II] or a salt thereof used as a starting material in the method of this invention can be produced in the following manner. Thus, by any of the processes described in Belgian Pat. No. 823861, French Pat. No. 7442914, Greek Pat. No. 60395, French patent application laid-open No. 2301528, Belgian Pat. No. 838833 and Dutch patent application laid-open No. 7601902, etc. or any process analogous thereto, a compound of the following formula [III] or a salt thereof is prepared in the first place and this compound [III] or a salt thereof is further reacted with a thiolating agent.

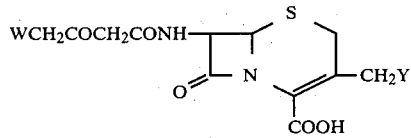

[wherein W and Y have the meanings respectively defined hereinbefore]

The term thiolating agent means a substance which is able to introduce the group RS- into [III] to give [II]. Thus, it may for instance be a thiolating agent which can be prepared by any of such known procedures as reacting a thiol (RSH; R is as previously defined) with, for example, halogen, N-halosuccinimide or N-halophthalimide or reacting a disulfide (RSSR, R is as previously defined) with halogen [these and other known procedures are described in Reid E. E.: Organic Chemistry of Bivalent Sulfur, Vol. 1, pp. 263–271; Yasuo Abe, Takeshige Nakabayashi and Jitsuo Tsuwgi: Bulletin of the Chemical Society of Japan, Vol. 46, pp. 1898–1899 (1973); Wilhelm Groebel: Chemische Berichte, 93, 284 (1960), 92, 2887 (1959); etc.]. Such a thiolating agent need not necessarily be an isolated substance but the reaction product mixture as such may be directly employed.

The thiolation reaction is generally carried out by admixing each molar equivalent of a compound of formula [III] or a salt thereof with 1 to 4 molar equivalents of said thiolating agent and 1 to 5 molar equivalents of an organic base in a solvent at a temperature from $-10°$ C. to $+40°$ C. The solvent is preferably such that it will not interfere with the thiolation reaction and, moreover, will at least partially dissolve the substrate compound [III] and thiolating agent. As such solvent, one of the solvents mentioned for use in the reaction of [II] with thiourea may be employed with advantage. The organic base is preferably a tertiaryamine such as trimethylamine, triethylamine, pyridine, N,N-dimethylaniline, N,N-dimethylbenzylamine, N-methylmorpholine, etc. This reaction yields [II] which is then subjected to the next reaction either as it is present in the reaction mixture or after having been summarily separated from the reaction mixture by procedures known per se.

METHOD 2

The contemplated compound [I] of this invention can also be produced by reacting a compound of the formula:

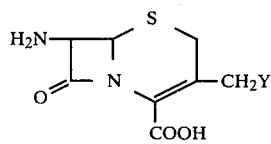

[wherein Y is as previously defined] or a salt thereof with a carboxylic acid which has the formula:

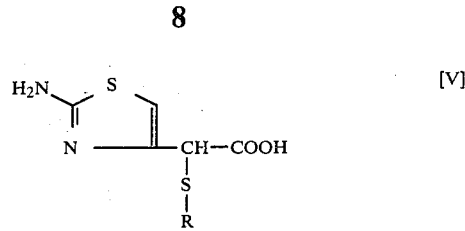

[wherein R is as previously defined], or a reactive derivative thereof.

This reaction is generally conducted by procedures known per se for acylating 7-aminocephalosporin derivatives [for example, by the procedures described in British Pats. No. 966221, No. 982252 and No. 986209; U.S. Pat. No. 3217000, No. 3270009, No. 3560489 and No. 3222363; etc.] or a procedure analogous to any of those known procedures. By way of illustration, the carboxylic acid of general formula [V] is reacted with compound [IV] or a salt thereof (as mentioned in connection with [I]), the former being any of the free carboxylic acid [V], the alkali or alkaline earth metal salt of [V] (e.g. sodium, potassium, calcium, etc. salts), organic amine salt of [V] (e.g. trimethylamine, pyridine, etc. salts) and reactive derivatives of [V] (e.g. acid halide (e.g. acid chloride, acid bromide, etc.), acid anhydride, mixed acid anhydride, active amide, activated ester, etc.). As examples of said activated esters there may be mentioned p-nitrophenyl ester, 2,4-dinitrophenyl ester, pentachlorophenyl ester, N-hydroxysuccinimide ester and N-hydroxyphthalimide ester. Examples of said mixed acid anhydride include mixed acid anhydrides with carbonic acid monoesters such as carbonic acid monomethyl ester, carbonic acid monoisobutyl ester, etc. and mixed acid anhydrides with lower alkanoic acids which may be substituted by halogen, such as pivalic acid, trichloroacetic acid, etc. When the carboxylic acid [V] is used as the free acid or in the form of a salt, an appropriate condensing agent is concomitantly employed. As the condensing agent there may be used N,N'-disubstituted carbodiimides (i.e. N,N'-dicyclohexylcarbodiimide, etc.), azolide compounds (i.e. N,N'-carbonylimidazole, N,N'-thionyldiimidazole, etc.), N-ethoxycarbonyl-2-ethoxy-1,2-dihydroquinoline, phosphorus oxychloride, alkoxyacetylene, 2-halogenopyridinium salts (e.g. 2-chloropyridiniummethyliodide, 2-fluoropyridiniummethyliodide, etc.) and so on. When such a condensing agent is employed, the reaction apparently proceeds via the formation of a reactive derivative of the carboxylic acid [V]. This reaction is generally conducted in a suitable solvent. As said solvent there may be frequently used halogenated hydrocarbons such as chloroform, methylene dichloride, etc.; ethers such as tetrahydrofuran, dioxane, etc.; and such other solvents as dimethylformamide, dimethylacetamide, acetone and water, as well as mixtures of such solvents. To each mole of compound [IV] or a salt thereof, the acrylating agent [V] or a reactive derivative thereof is employed normally in a proportion of about 1 to several molar equivalents. This reaction is generally conducted at a temperature from $-50°$ C. to $+40°$ C., Following this acylation reaction, the amino-protecting group may be removed, if necessary.

This removal of amino-protecting group can be effected generally by the known procedures (e.g. the methods described in British Pat. No. 1453049, French Pat. No. 2241318 and Pure and Applied Chemistry, 7, 335 (1963) or any procedure analogous thereto. The compound [I] thus obtained can be isolated and purified by procedures known per se.

METHOD 3

The compound [I] or a salt thereof of this invention in which Y is —S—Het can also be produced by reacting the compound obtained by the above-described Method 1 or Method 2 wherein Y is acyloxy with a nitrogen-containing heterocycle-thiol[Het-SH]. If attention is solely focused on the 3-position of the cephem ring, this method is essentially analogous to a nucleophilic replacement reaction of the 3-acyloxy group as described in the prior art scientific and patent literature (e.g. C. F. Murphy and J. A. Webber: Cephalosporins and Penicillins: Chemistry and Biology, E. H. Flynn, Ed., Academic Press, New York, N.Y. 1972, Chap. IV; U.S. Pat. No. 3278531, British Pat. No. 1012943, No. 1030630 and No. 1028563 and U.S. Pat. No. 3218318) and, therefore, this method can be carried out by the same procedures or any procedure analogous thereto.

Thus, this reaction is carried out by reacting a compound [I] wherein Y is acyloxy or a salt thereof with a nitrogen-containing heterocycle-thiol[Het—SH] or a reactive derivative in the thiol function thereof. The reaction is advantageously conducted by admixing the two materials in a solvent at room temperature or under heating. As the salt of compound [I] wherein Y is acyloxy, there may be used alkalimetal salts and alkaline earth metal salts of the types mentioned hereinbefore as salts of [I]. The reactive derivative in the thiol function of Het—SH may for instance be the alkali metal salt, such as the sodium or potassium salt. As the solvent, there may be used e.g. water, acetone, chloroform, nitrobenzene, dichloromethane, dimethylformamide, methanol, ethanol, tetrahydrofuran, dimethylsulfoxide or a suitable mixture of such solvents. When the starting materials are free compounds, satisfactory results are obtained in many cases if the pH of the reaction system is maintained in the weakly basic to neutral region throughout the reaction period with the addition of a suitable amount of alkali metal hydroxide (e.g. sodium hydroxide or potassium hydroxide), alkali metal carbonate (e.g. sodium carbonate or potassium carbonate), an alkali metal hydrogen carbonate (e.g. sodium hydrogen carbonate or potassium hydrogen carbonate) or the like. The reaction is generally carried out by admixing a compound [I] wherein Y is acyloxy or a salt thereof with 1 to 2 equivalents of Het—SH or a salt thereof in said solvent and allowing the reaction to proceed at room temperature or under heating at a temperature of up to 100° C. The product compound [I] or a salt thereof can be isolated and purified in the same manner as mentioned hereinbefore, e.g. by means of procedures known per se.

The compound [I] or a salt thereof produced by any of the methods of this invention may undergo tautomerization to assume both the thiazole and thiazoline forms.

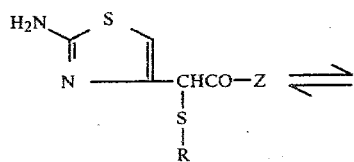

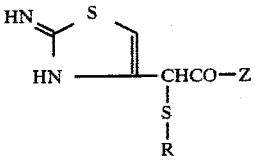

[wherein Z is

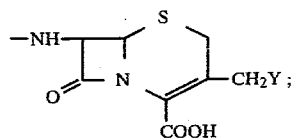

the other symbols as previously defined]

Although this invention encompasses all the aforesaid tautomeric forms, each of the compounds is herein designated and shown by reference to the thiazole form for convenience' sake.

The method fo this invention will hereinafter be described in further detail by way of examples. In these examples, NMR spectra are determined with a Varian XL-100 (100 MHz), EM-390 (90 MHz) or T-60 (60 MHz) spectrophotometer wih tetramethylsilane as the standard and the chemical shifts δ are expressed in ppm. In the spectra, s denotes a singlet, d a doublet, t a triplet, q a quartet, m a multiplet, dd a double doublets, J a coupling constant. IR means an infrared absorption spectrum.

REFERENCE EXAMPLE 1

Production of N-(2-carboxyphenylthio)succinimide.-triethylamine salt

While a solution of 0.462 g thiosalicylic acid, 0.6 g triethylamine and 8 ml methylene chloride is stirred under ice-cooling, 0.4 g of N-chlorosuccinimide is added. The mixture is stirred for 30 minutes and the resulting crystals are recovered by filtration.

By this procedure is obtained the above-indicated compound. Yield 1 g. m.p. 148°–150° C. (decompn.) IR (KBr, cm$^{-1}$): 2975, 2930, 2600, 2500, 1715, 1590, 1575 NMR (90 MHz, d$_6$-DMSO, δ):1.18(t, J=5 Hz, CH$_3$), 2.55(s, —CH$_2$CH$_2$—), 2.98(q, J=5 Hz, —C$\underline{H_2}$—CH$_3$), 7.0–7.6, 7.8–8.0 (m, C$_6$H$_4$—)

Elemental analysis, for C$_{11}$H$_9$NO$_4$S.(C$_2$H$_5$)$_3$N Calcd. C, 57.94; H, 6.87; N, 7.95. Found C, 56.19; H, 7.80; N, 8.23.

EXAMPLE 1

Production of sodium 7-[2-(2-aminothiazol-4-yl)-2-methylthioacetamido]-3-(1-methyl-1H-tetrazol-5-yl)thiomethyl-3-cephem-4-carboxylate While a solution of 2.0 g 7-(4-chloro-3-oxobutyrylamino)-3-(1-methyl-1H-tetrazol-5-yl)thiomethyl-3-cephem-4-carboxylic acid and 1.0 g triethylamine in 30 ml of methylene chloride is stirred under ice-cooling, 0.504 g of methanethiosulfonic acid S-methyl is added. The mixture is stirred for one hour. The reaction mixture is stirred vigorously with 10 ml of 10% phosphoric acid and the organic layer is taken, dried and distilled under reduced pressure to remove the solvent. The residue is stirred with ether and the powdery product (1.2 g) is recovered by filtration. The powders are dissolved in 4 ml of dimethylacetamide, followed by addition of 0.228 g of thiourea. The mixture is stirred for 3 hours and, then ether is added. The resulting powders are recovered by filtration and dissolved in 10 ml of a 10% aqueous solution of sodium hydrogen carbonate. The solution is run onto a chromatographic column of polystyrene resin (Amberlite ®XAD-2, Rohm and Haas Co.) and elution is carried out with water and 5% ethanol in that order. The fractions rich in the desired compound are pooled and lyophilized. By the above procedure is obtained the above-indicated compound. Yield 0.35 g. IR (KBr, cm$^{-1}$): 1765, 1610, 1520, 1395, 1360 NMR (100 MHz, D$_2$O, δ): 2.17 & 2.21(each s, SCH$_3$), 3.42 & 3.77; 3.46 & 3.99(each ABq, J=18 Hz, 2—CH$_2$), 4.10 & 4.35 (ABq, J=13 Hz, 3—CH$_2$), 5.12 & 5.13(each , J=4.5 Hz, 6—H), 5.64 & 5.66(each d, J=4.5 Hz, 7—H), 6.68 & 6.70(each s, thiazole 5—H)

Elemental analysis, for C$_{16}$H$_{17}$N$_8$O$_4$S$_4$Na.2H$_2$O: Calcd. C, 33.56; H, 3.70; N, 19.57. Found C, 33.53; H, 3.54; N, 19.57.

EXAMPLE 2

Production of disodium 7-[2-(2-aminothiazol-4-yl)-2-(2-carboxyphenylthio)acetamido]-3-(2-methyl-1,3,4-thiadiazol-5-yl)thiomethyl-3-cephem-4-carboxylate (1) While a mixed solution of 0.462 g thiosalicylic acid and 0.6 g triethylamine in 8 ml of methylene chloride is cooled with ice, 0.4 g of N-chlorosuccinimide is added. The mixture is stirred for 5 minutes. Separately, a solution of 1 g 7-(4-chloro-3-oxobutyrylamino)-3-(2-methyl-1,3,4-thiadiazol-5-yl)thiomethyl-3-cephem-4-carboxylic acid and 0.6 g triethylamine in 15 ml of methylene chloride is ice-cooled and the above reaction mixture is added at one time and stirred for 2 minutes. This reaction mixture is stirred vigorously with 3 ml of 50% phosphoric acid and 7 ml of saturated aqueous sodium chloride. The organic layer is taken and the water layer is extracted with ethyl acetate. The organic layers are combined and dried. The solvent is then distilled off under reduced pressure and the residue is stirred with ether. By the above procedure is obtained 7-[4-chloro-3-oxo-2-(2-carboxyphenylthio)butyrylamino]-3-(2-methyl-1,3,4-thiadiazol-5-yl)thiomethyl-3-cephem-4-carboxylic acid as powders. Yield 1.4 g. IR (KBr, cm$^{-1}$): 1770, 1700, 1590, 1520, 1380, 1230, 750 NMR (90 MHz, d$_6$-DMSO, δ): 2.67(s, thiadiazole—CH$_3$), 3.40 & 3.67(ABq, J=18 Hz, 2—CH$_2$), 4.17 & 4.52(ABq, J=13.5 Hz, 3—CH$_2$), 4.48(s, ClCH$_2$CO), 5.02(d, J=4.5 Hz, 6—H), 5.58(dd, J=4.5, 9.0 Hz, 7H), 8.67(d, J=9 Hz, CONH—)

(2) In 5 ml of dimethylacetamide are dissolved 1.4 g of 7-[4-chloro-3-oxo-2-(2-carboxyphenylthio)butyrylamino]3-(2-methyl-1,3,4-thiadiazol-5-yl)thiomethyl-3-cephem-4-carboxylic acid and 0.228 g of thiourea, and the solution is stirred at room temperature for 2 hours. The reaction mixture is allowed to stand in a refrigerator for 72 hours, at the end of which time ether is added. The resulting powders are recovered by filtration and dissolved in 3.4 ml of 10% aqueous sodium hydrogen carbonate. The solution is run onto a chromatographic column of polystyrene resin (XAD-2, Rohm and Haas Co.), elution being carried out with water. The fractions rich in the contemplated compound are pooled and run onto a chromatographic column of dextran gel (Sephadex ®LH-20, Pharmacia Fine Chemicals), elution being carried out with water. The fractions rich in the desired compound are pooled and lyophilized. By the above procedure is obtained the above-indicated compound. Yield 0.276 g. IR (KBr, cm$^{-1}$): 1760, 1590, 1380 NMR (90 MHz, d$_6$-DMSO, δ): 2.63(s, thiadiazole-2—CH$_3$), 4.32 & 4.52(ABq, J=13.5 Hz, 3—CH$_2$), 4.90(d, J=4.5 Hz, 6—H), 5.07(s, SCHCO), 5.48(m, 7—H), 6.45(s, thiazole 5—H), 6.8–7.3 & 7.6–7.9(m, C$_6$H$_4$ & NH$_2$), 9.15(d, J=9 Hz, CONH—).

Elemental analysis, for C$_{23}$H$_{18}$N$_6$O$_6$S$_5$Na$_2$.1.5H$_2$O: Calcd. C, 39.03; H, 2.99; N, 11.87. Found C, 39.11; H, 3.08; N, 10.68.

EXAMPLE 3

The following compounds are produced in the same manner as Example 2.

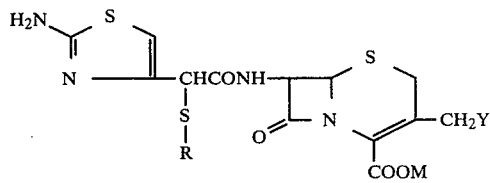

| No. | R | Y | M | IR(KBr,cm$^{-1}$) | NMR, δ |
|---|---|---|---|---|---|
| 1 | ⌬-CO$_2$Na | —OCOCH$_3$ | Na | 1760, 1600, 1380, 1240 | (100MHz d$_6$DMSO); 2.02(s,OCOCH$_3$), 3.1~3.5(m,2-H), 4.6 ~ 5.1(m,3-CH$_2$ & 6-H), 5.12 (s,—SCHCO), 5.5(broad,7-H), 6.52(s, thiazole 5-H), 6.9 ~ 7.2, 7.6 ~ 7.9(m,NH$_2$ & C$_6$H$_4$), 9.13(d,J = 8.0Hz,CONH—) |
| 2 | ⌬-CO$_2$Na | -S-(N=N, N-CH$_3$) | Na | 1760, 1600, 1395 | (100MHz d$_6$DMSO); 3.93(s,—CH$_3$), 3.3 ~ 3.7 (m,2-H), 4.27 & 4.48(ABq,J = 12Hz,3-CH$_2$), 4.94(d,J = 4.5 Hz,6-H), 5.13(s,—SCHCO), 5.55(m,7-H), 6.52(s,thiazole 5-H),6.8~7.4 & 7.6 ~ 7.9(m,C$_6$H$_4$), 9.13(d,J = 8Hz, CONH—) |
| 3 | ⌬-CO$_2$Na | -S-(N=N, S)-H | Na | 1760, 1595, 1380, 1060, 755 | (90MHz d$_6$DMSO); 4.5(broad s,3-CH$_2$), 4.91 (d,J = 4.5Hz,6-H), 5.10(s,—SCHCO), 5.5 & 5.6(each m,7-H), 6.44(s,thiazole 5-H), 6.7 ~ 7.3, 7.6 ~ 8.0(m,H$_2$N & C$_6$H$_4$), 9.16 & 10.1(each d,J = 8.0Hz,CONH—) |

|     |                                                                                   | Elemental analysis |      |       |       |      |       |
|-----|-----------------------------------------------------------------------------------|--------|------|-------|-------|------|-------|
|     |                                                                                   | Calcd. |      |       | Found |      |       |
| No. | Molecular formula                                                                 | C      | H    | N     | C     | H    | N     |
| 1   | $C_{22}H_{18}N_4O_8S_3Na_2 \cdot H_2O$                                            | 42.17  | 3.22 | 8.94  | 42.02 | 3.75 | 8.74  |
| 2   | $C_{22}H_{18}N_8O_6S_4Na_2 \cdot 2H_2O$                                           | 37.71  | 3.16 | 15.99 | 37.68 | 3.65 | 14.70 |
| 3   | $C_{22}H_{16}N_6O_6S_4Na_2 \cdot 2.5H_2O$                                         | 38.88  | 3.11 | 12.36 | 38.86 | 3.78 | 11.20 |

EXAMPLE 4

Production of sodium 7-[2-(2-aminothiazol-4-yl)-2-(2-chlorophenylthio)acetamido]-3-(1-methyl-1H-tetrazol-5-yl)thiomethyl-3-cephem-4-carboxylate In 15 ml of methylene chloride are dissolved 1.0 g of 7-(4-chloro-3-oxobutyrylamino)-3-(1-methyl-1H-tetrazol-5-yl)thiomethyl-3-cephem-4-carboxylic acid and 0.505 g of triethylamine and while the solution is cooled with ice, 0.5 g of N-(2-chlorophenylthio)succinimide is added. The mixture is stirred for 5 minutes. This reaction mixture is shaken with 1 ml of 50% phosphoric acid, 4 ml of water and 5 ml of tetrahydrofuran. The organic layer is taken, dried and concentrated to dryness under reduced pressure. The residue is stirred with ether and the resulting powders are collected by filtration. The powders are dissolved, together with 0.152 g of thiourea, in 2 ml of dimethylacetamide and the mixture is stirred at room temperature for 3 hours. The reaction mixture is stirred with ether, the supernatant is discarded by decanting, the residue is stirred with water and the powdery precipitate is collected by filtration and dissolved in 3.4 ml of 10% sodium hydrogen carbonate. The solution is run onto a chromatographic column of polystyrene resin (Amberlite ®XAD-2, Rohm and Haas Co.) and elution is carried out with water, 10% ethanol, 20% ethanol and 30% ethanol in the order mentioned.

The fractions rich in the desired compound are pooled and lyophilized. By this procedure is obtained the above-indicated compound. Yield 0.35 g. IR (KBr, $cm^{-1}$): 1760, 1600, 1520, 1480, 1390, 1360, 750 NMR (100 MHz, $d_6$—DMSO, δ): 3.95(s, tetrazole—CH$_3$), 4.27 & 4.44(ABq, J=14 Hz, 3—CH$_2$), 4.99(d, J=4.5 Hz, 6—H), 5.27(s, SCHCO), 5.55 & 5.77(each dd, J=4.5 & 8 Hz, 7—H), 6.54 & 6.56(each s, thiazole 5—H), 7.0-7.6(m, NH$_2$ & C$_6$H$_4$), 9.0, 9.24 & 10.04(each d, J=8 Hz, CONH—). NMR (100 MHz, $d_6$—DMSO—D$_2$O, δ): 3.43 & 3.67(ABq, J=18 Hz, 2—CH$_2$), 3.96(s, tetrazole—CH$_3$), 4.33(broad s, 3—CH$_2$), 4.97(d, J=4.5 Hz, 6—H), 5.57(d, J=4.5 Hz, 7—H), 6.56 & 6.58(each s, thiazole 5-H), 7.2-7.6(m, C$_6$H$_4$)

Elemental analysis, for $C_{21}H_{18}ClN_8O_4S_4Na \cdot 0.5H_2O$: Calcd. C, 39.28; H, 2.98; N, 17.45. Found C, 39.19; H, 3.01; N, 17.49.

EXAMPLE 5

The following compounds are produced in the same manner as Example 4.

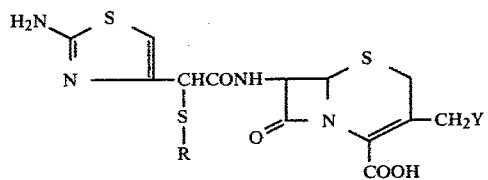

| No. | R | Y | M | IR(KBr,cm$^{-1}$) | NMR, δ |
|---|---|---|---|---|---|
| 1 | 3-Cl-C$_6$H$_4$— | -S-(1-methyl-tetrazol-5-yl) | Na | 1760, 1600, 1515, 1480, 1395, 1360, 1220, 1180, 780 | (100MHz,d$_6$DMSO); 3.95(s,CH$_3$), 4.27 & 4.47(ABq,J = 13Hz,3-CH$_2$), 6.50 & 6.53(each s,thiazole 5-H), 7.06 (broad s,H$_2$N), 7.3 ~ 7.5(m,C$_6$H$_4$), 8.92, 9.12 & 10.01(each d,J = 8.0Hz, CONH—) |
| 2 | 4-F-C$_6$H$_4$— | -S-(1-methyl-tetrazol-5-yl) | Na | 1760, 1600, 1510, 1480, 1390, 1350, 1220, 830 | (100MHz,d$_6$DMSO); 3.40(one of ABq; J = 18Hz,2-H), 3.95(s,CH$_3$), 4.27 & 4.47(ABq,J = 13Hz,3-CH$_2$), 4.98(d,J = 4.5Hz,6-H), 5.02(s,—SCHCO), 5.53(d, d,J = 4.5,8.0Hz,7-H), 6.44 & 6.48 (each s,thiazole 5H),7.0 ~ 7.6(m, H$_2$N & C$_6$H$_4$), 8.86 & 9.04(each d, J = 8.0Hz,CONH—) |
| 3 | 4-Br-C$_6$H$_4$— | -S-(1-methyl-tetrazol-5-yl) | Na | 1760, 1600, 1510, 1470, 1385, 1365, 1010, 810 | (100MHz,d$_6$DMSO); 3.41(one of ABq, J = 18Hz,2-H), 3.95(s,CH$_3$), 4.27 & 4.46(ABq,J = 13Hz,3-CH$_2$), 4.97(d,J = 4.5Hz,6-H), 5.13(s,—SCHCO), 5.55 (broad 7-H),6.48 & 6.51(each s, thiazole 5-H), 7.04(broad H$_2$N), 7.33 & 7.50(ABq,J = 8.0Hz, —C$_6$H$_4$—Br), 8.92, 9.11(each d,J = 8.0Hz,CONH—) |

| No. | R | Y | M | IR(KBr,cm⁻¹) | NMR, δ |
|---|---|---|---|---|---|
| 4 | 4-Cl-C₆H₄- | -S-(1-methyl-tetrazol-5-yl) | Na | 1760, 1605, 1510, 1475, 1390, 1355 | (100MHz,D₂O); 3.0 ~ 3.9(broad, 2-H), 3.9 ~ 4.5(broad,3CH₂), 3.96(s,—CH₃), 5.02(broad,6-H), 5.6(broad,7-H), 6.5 (broad, thiazole 5-H), 6.9 ~ 7.5(broad, C₆H₄) |
| 5 | C₆H₅- | -S-(1-methyl-tetrazol-5-yl) | Na | 1715, 1675, 1610, 1515, 1390 | (100MHz,D₂O); 3.29 & 3.62(ABq,J = 18Hz, 2-H), 3.92(s,CH₃), 5.0(d,J = 4.5Hz,6-H), 5.58(broad s, SCHCO), 6.42 & 6.45 (each s, thiazole 5-H), 7.10 & 7.27 (broad s, —C₆H₅) |

| No. | Molecular formula | Calcd. C | Calcd. H | Calcd. N | Found C | Found H | Found N |
|---|---|---|---|---|---|---|---|
| 1 | C₂₁H₁₈ClN₈O₄S₄Na · 2.5H₂O | 37.34 | 3.11 | 16.34 | 37.69 | 3.28 | 16.37 |
| 2 | C₂₁H₁₈FN₈O₄S₄Na · 2.5H₂O | 38.11 | 3.50 | 16.94 | 37.79 | 2.90 | 16.89 |
| 3 | C₂₁H₁₈BrN₈O₄S₄Na · 3H₂O | 34.47 | 3.31 | 15.32 | 34.76 | 3.23 | 15.14 |
| 4 | C₂₁H₁₈ClN₈O₄S₄Na · 1.5H₂O | 38.21 | 3.21 | 16.97 | 38.39 | 3.57 | 16.54 |
| 5 | C₂₁H₁₉N₈O₄S₄Na · 3H₂O | 38.64 | 3.86 | 17.17 | 38.70 | 3.36 | 18.62 |

EXAMPLE 6

Production of disodium 7-[2-(2-aminothiazol-4-yl)-2-(2-carboxy-5-chlorophenylthio)acetamido]-3-(1-methyl-1H-tetrazol-5-yl)thiomethyl-3-cephem-4-carboxylate In 10 ml of methylene chloride is suspended 0.725 g of 2-mercapto-4-chlorobenzoic acid, and under ice-cooling, 0.532 g of N-chlorosuccinimide and 1 ml of dimethylformamide are added. The mixture is stirred under ice-cooling for 10 minutes.

Separately, 1 g of 7-(4-chloro-3-oxobutyrylamino)-3-(1-methyl-1H-tetrazol-5-yl)thiomethyl-3-cephem-4-carboxylic acid and 1 g of triethylamine are dissolved in 20 ml of methylene chloride, and while the solution is cooled with ice, the above reaction mixture is added at one time. The mixture is stirred for 2 minutes, at the end of which time it is shaken vigorously with 3 ml of 50% phosphoric acid and 7 ml of saturated aqueous sodium chloride. The organic layer is taken and subjected to dehydration with anhydrous magnesium sulfate. After filtration of the magnesium sulfate, 0.228 g of thiourea and 4 ml of dimethylformamide are added to the filtrate. The methylene chloride is then distilled off under reduced pressure and the solution of the residue in dimethylformamide is stirred at room temperature for one hour and, then, allowed to stand in a refrigerator for 15 hours. The solution is washed with ether, followed by the addition of water. The resulting powders are collected by filtration and dissolved in 10 ml of 5% sodium hydrogen carbonate. The solution is run onto a chromatographic column of polystyrene resin (XAD-2, Rohm and Haas Co.), elution being carried out with water and 5% ethanol. The fractions rich in the desired compound are pooled and lyophilized. By this procedure is obtained the above-indicated compound. Yield 0.17 g. IR (KBr, cm⁻¹): 1760, 1595, 1520 NMR (90 MHz, d₆—DMSO, δ): 4.20 & 4.46(ABq, J=12 Hz, 3—CH₂), 4.91(d, J=4 Hz, 6-H), 5.4-5.8(m, 7—H), 6.50(s, thiazole 5—H), 6.7-7.9(m, NH₂ & C₆H₃), 9.01 & 10.0(each d, J=9 Hz, CONH—)

Elemental analysis, for C₂₂H₁₇ClN₈O₆S₄Na₂·3H₂O: Calcd. C, 35.08; H, 3.08; N, 14.88. Found C, 34.38; H, 3.37; N, 15.71.

EXAMPLE 7

The following compounds are produced in the same manner as Example 6.

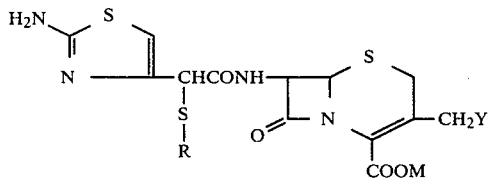

| No. | R | Y | M | IR(KBr,cm⁻¹) | NMR, δ |
|---|---|---|---|---|---|
| 1 | 2-CO₂Na-5-Cl-C₆H₃- | -S-(1-methyl-tetrazol-5-yl) | Na | 1760, 1600, 1520, 1400, 1360, 815, 760, 700 | (100MHz d₆DMSO); 3.94(s,CH₃), 4.27 & 4.48(ABq,J = 12.0Hz,3-CH₂), 4.96(d,J = 4.5Hz,6-H), 5.14(s,—SCHCO), 5.55(broad, 7-H), 6.51(s,thiazole,5-H), 6.8 ~ 7.4, 7.6 ~ 7.9(m,H₂N & C₆H₃), 9.06 & 9.13(each d,J = 8Hz,CONH—) |

-continued

| No. | R | Y | M | IR(KBr,cm$^{-1}$) | NMR, δ |
|---|---|---|---|---|---|
| 2 | Cl-C$_6$H$_3$(CH$_3$)-CO$_2$Na | -S-C(=N-N=N-N(CH$_3$))- | Na | 1760, 1590, 1520, 1390 | (100MHz d$_6$DMSO); 3.94(s,CH$_3$), 4.34(broad S,3CH$_2$), 4.82 & 4.85(each d,J = 4.5Hz,6-H), 5.3(broad, 7-H), 5.38 & 5.40(each s, —SCHCO), 6.50(s,thiazole 5-H), 7.00 (broad s,H$_2$N—), 7.18 ~ 7.4(m,C$_6$H$_3$), 9.83 & 10.43(each d,J = 8.0Hz,CONH—) |
| 3 | Br-C$_6$H$_3$-CO$_2$Na | -S-C(=N-N=N-N(CH$_3$))- | Na | 1760, 1600, 1520, 1480, 1400, 1360 | (100MHz d$_6$DMSO); 3.95(s,CH$_3$), 4.27 & 4.47(ABq,J = 13Hz,3CH$_2$), 4.96(d,J =4.5Hz, 6-H), 5.16(s,—SCHCO), 5.55(broad, 7-H), 6.52(s,thiazole 5-H), 6.7 ~ 8.0(m,H$_2$N, C$_6$H$_3$), 9.08 & 9.16(each d,J = 8.0Hz, CONH—) |
| 4 | I-C$_6$H$_3$-CO$_2$Na | -S-C(=N-N=N-N(CH$_3$))- | Na | 1760, 1600, 1520, 1480, 1400, 1360, 815 | (100MHz,d$_6$DMSO); 3.94(s,CH$_3$), 4.28 & 4.47(ABq,J = 14Hz,3-CH$_2$), 4.95(d,J = 4.5Hz, 6-H), 5.12(s,—SCHCO), 5.55(m,7-H), 6.50 (s, thiazole 5-H), 7.0 ~ 7.2, 7.4 ~ 7.6, 8.0 ~ 8.2(m,H$_2$N,C$_6$H$_3$), 9.08(broad CONH—) |

| | | Elemental analysis | | | | |
|---|---|---|---|---|---|---|
| | | Calcd. | | | Found | |
| No. | Molecular formula | C | H | N | C | H | N |
| 1 | C$_{22}$H$_{17}$ClN$_8$O$_6$S$_4$Na$_2$ · 3.5H$_2$O | 34.67 | 3.17 | 14.70 | 34.50 | 3.37 | 16.29 |
| 2 | C$_{22}$H$_{17}$ClN$_8$O$_6$S$_4$Na$_2$ · 3H$_2$O | 35.08 | 3.08 | 14.88 | 35.01 | 3.31 | 14.60 |
| 3 | C$_{22}$H$_{17}$BrN$_8$O$_6$S$_4$Na$_2$ · 3H$_2$O | 33.13 | 2.90 | 14.05 | 32.73 | 3.09 | 14.58 |
| 4 | C$_{22}$H$_{17}$IN$_8$O$_6$S$_4$Na$_2$ · 3H$_2$O | 31.29 | 2.74 | 13.27 | 31.00 | 3.02 | 13.59 |

EXAMPLE 8

Production of 7-[2-(2-aminothiazol-4-yl)-2-(2-carboxyphenylthio)acetamido]-3-[1-(2-dimethylaminoethyl)-1H-tetrazol-5-yl]thiomethyl-3-cephem-4-carboxylic acid A solution of 0.9 g diketene and 10 ml methylene chloride is cooled to −30° C. and 1.6 g of bromine is added dropwise.

Separately, 2 g of N-chlorosuccinimide is added to a solution of 2.3 g thiosalicylic acid, 3 g triethylamine and 30 ml methylene chloride and the mixture is stirred under ice-cooling for 5 minutes. On the other hand, 3.4 g of 7-amino-3-[1-(2-dimethylaminoethyl)-1H-tetrazol-5-yl]thiomethyl-3-cephem-4-carboxylic acid and 3 g of triethylamine are dissolved in 50 ml of methylene chloride and while the solution is stirred under cooling at −30° C., the above solution of 4-bromo-3-oxobutyryl bromide is added. Then, 2 g of triethylamine is added to the mixture and the above suspension of N-(2-carboxyphenylthio)succinimide is further added. After a few minutes, 1.5 g of thiourea and 20 ml of dimethylformamide are added at one time. The methylene chloride is distilled off under reduced pressure and the residue is stirred at room temperature for 2 hours. The reaction mixture is washed with ether, water is added, and the mixture is run onto a chromatographic column of polystyrene resin (Amberlite ® XAD-2, Rohm and Haas Co.), elution being carried out with water and 5%, 10% and 20% alcohols in that order. The fractions rich in the desired compound are pooled, concentrated under reduced pressure and lyophilized. By the above procedure is obtained the above-indicated compound. Yield 1.93 g. IR (KBr, cm$^{-1}$): 1765, 1600, 1480, 1380 NMR (90 MHz, d$_6$—DMSO, δ): 2.20(s, N—(CH$_3$)$_2$), 2.73(t, J=6 Hz,

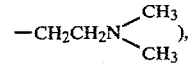

3.5(broad, 2—H), 4.36(t, J=6 Hz,

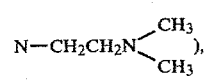

4.93(d, J=4.5 Hz, 6—H), 6.46(s, thiazole 5—H), 6.9–7.5, 7.7–7.9(m, H$_2$N & C$_6$H$_4$), 8.96, 9.18, 10.03 (each d, J=9 Hz, CONH—).

Elemental analysis, for C$_{25}$H$_{27}$N$_9$O$_6$S$_4$.1.2 N(C$_2$H$_5$)$_3$.2H$_2$O: Calcd. C, 46.30; H, 5.91; N, 17.10. Found C, 46.35; H, 5.93; N, 16.88.

The following table shows the minimal inhibitory concentrations (MIC) of some representative cephalosporin derivatives of this invention as obtained in the foregoing examples against a variety of bacteria, along with the corresponding MICs of the commercially available and clinically accepted cephalosporins, namely Cephalothin=sodium 7-(2-thienylacetamido)-3-acetoxymethyl-3-cephem-4-carboxylate; Cephaloridine=7-(2-thienylacetamido)-3-(1-pyridyl)methyl-3-cephem-4-carboxylic acid betaine; and Cefazolin=sodium 7-(1H-tetrazol-1-yl)acetamido-3-(2-methyl-1,3,4-thiadiazol-5-yl)thiomethyl-3-cephem-4-carboxylate [The New England Journal of Medicine 294, 24(1976) and Journal of Pharmaceutical Science 64, 1899 (1975)].

Minimal inhibitory concentrations (Tables 1 to 4)
Method: Serial agar dilution
Medium: TSA

TABLE 1

(mcg/ml)

| Test compound | Gram-positive bacteria | | Gram-negative bacteria | | | | | | |
|---|---|---|---|---|---|---|---|---|---|
| | S. aureus 209 P | S. aureus 1840 | E. coli NIHJ JC-2 | E. coli O-111 | E. coli T-7 | K. pneumoniae DT | K. pneumoniae GN 3835 | S. marscecens IFO 12648 | S. marscecens TN 24 |
| Cephalothin | 0.20 | 0.39 | 12.5 | 3.13 | 100 | 1.56 | 12.5 | >100 | >100 |
| Cephaloridine | 0.05 | 0.39 | 3.13 | 1.56 | >100 | 1.56 | 12.5 | >100 | >100 |
| Cefazolin | 0.39 | 1.56 | 1.56 | 1.56 | 100 | 1.56 | 6.25 | >100 | >100 |
| Example 1 | 1.56 | 1.56 | 0.39 | 0.1 | 25 | 0.2 | 0.78 | 6.25 | 0.78 |
| Example 2 | 6.25 | 12.5 | 0.39 | ≦0.05 | 3.13 | 0.1 | 0.39 | 0.78 | 0.2 |
| Example 3-1 | 25 | 12.5 | 0.39 | 0.05 | 3.13 | 0.2 | 0.39 | 1.56 | 0.78 |
| Example 3-2 | 25 | 12.5 | 0.2 | 0.05 | 3.13 | 0.1 | 0.2 | 0.78 | 0.2 |
| Example 3-3 | 6.25 | 12.5 | 0.39 | ≦0.05 | 3.13 | 0.1 | 0.39 | 0.78 | 0.2 |
| Example 4 | 0.39 | 0.39 | 1.56 | 0.39 | 25 | 0.39 | 3.13 | 6.25 | 6.25 |
| Example 5-1 | 0.39 | 0.78 | 3.13 | 0.78 | 50 | 0.78 | 3.13 | 6.25 | 6.25 |
| Example 5-2 | 0.78 | 0.78 | 3.13 | 0.78 | 25 | 0.78 | 6.25 | 12.5 | 12.5 |

TABLE 2

(mcg/ml)

| Test Compound | Gram-positive bacteria | | Gram-negative bacteria | | | | | | |
|---|---|---|---|---|---|---|---|---|---|
| | S. aureus 209 P | S. aureus 1840 | E. coli NIHJ JC-2 | E. coli O-111 | E. coli T-7 | K. pneumoniae DT | K. pneumoniae GN 3835 | S. marscecens IFO 12648 | S. marscecens TN 24 |
| Example 5-3 | 0.39 | 1.56 | 3.13 | 0.78 | 50 | 0.78 | 6.25 | 12.5 | 12.5 |
| Example 5-4 | 0.39 | 0.78 | 3.13 | 0.78 | 50 | 0.39 | 3.13 | 6.25 | 6.25 |
| Example 5-5 | 0.39 | 0.78 | 0.78 | ≦0.2 | 3.13 | ≦0.2 | 1.56 | 6.25 | 3.13 |
| Example 6 | 3.13 | 3.13 | 1.56 | 0.2 | 12.5 | 0.2 | 3.13 | 3.13 | 6.25 |
| Example 7-1 | 1.56 | 3.13 | 0.78 | 0.1 | 6.25 | ≦0.05 | 0.78 | 1.56 | 1.56 |
| Example 7-2 | 6.25 | 12.5 | 1.56 | 0.2 | 6.25 | 0.1 | 1.56 | 3.13 | 1.56 |
| Example 7-3 | 3.13 | 3.13 | 1.56 | 0.1 | 12.5 | ≦0.05 | 1.56 | 1.56 | 3.13 |
| Example 7-4 | 3.13 | 3.13 | 1.56 | 0.2 | 12.5 | 0.1 | 1.56 | 1.56 | 3.13 |
| Example 8 | 12.5 | 25 | 0.2 | ≦0.05 | 3.13 | ≦0.05 | 0.39 | 0.78 | 0.2 |

TABLE 3

(mcg/ml)

| Test compound | Gram-negative bacteria | | | | | | | | |
|---|---|---|---|---|---|---|---|---|---|
| | P. vulgaris IFO 3988 | P. vulgaris CTN 4413 | P. mirafilis CTN 4359 | P. morganii IFO 3168 | P. rettgeri TN 338 | P. rettgeri CTN 4733 | F. cloacae IFO 12937 | C. freundii GN 99 | C. freundii GN 1706 |
| Cephalothin | 1.56 | >100 | 3.13 | >100 | 1.56 | >100 | >100 | 25 | >100 |
| Cephaloridine | 6.25 | >100 | 6.25 | >100 | 1.56 | >100 | >100 | 50 | >100 |
| Cephazolin | 3.13 | >100 | 6.25 | 100 | ≦0.2 | 100 | >100 | 12.5 | >100 |
| Example 1 | 0.2 | >100 | 0.78 | 0.39 | ≦0.05 | 0.39 | 3.13 | 0.39 | 0.78 |
| Example 2 | ≦0.05 | 0.2 | 0.2 | 0.2 | ≦0.05 | 0.2 | 1.56 | 0.39 | 0.78 |
| Example 3-1 | ≦0.012 | 0.39 | 0.05 | 0.2 | 0.024 | 0.2 | 25 | 0.39 | 0.78 |
| Example 3-2 | 0.024 | 0.39 | 0.1 | 0.1 | ≦0.012 | 0.2 | 3.13 | 0.2 | 0.39 |
| Example 3-3 | ≦0.05 | 0.2 | 0.1 | ≦0.05 | ≦0.05 | 0.2 | 1.56 | 0.39 | 0.78 |
| Example 4 | 3.13 | 25 | 3.13 | 3.13 | 0.39 | 0.78 | 3.13 | 0.78 | 1.56 |
| Example 5-1 | 3.13 | 25 | 3.13 | 1.56 | 0.39 | 0.78 | 6.25 | 1.56 | 3.13 |
| Example 5-2 | 6.25 | 100 | 3.13 | 3.13 | 0.39 | 0.78 | 12.5 | 1.56 | 3.13 |

TABLE 4

(mcg/ml)

| Test compound | Gram-negative bacteria | | | | | | | | |
|---|---|---|---|---|---|---|---|---|---|
| | P. vulgaris IFO 3988 | P. vulgaris GN 4413 | P. mirabilis GN 4359 | P. morganii IFO 3168 | P. rettgeri TN 338 | P. rettgeri GN 4733 | E. cloacae IFO 12937 | C. freundii GN 99 | C. freundii GN 1706 |
| Example 5-3 | 6.25 | 50 | 3.13 | 1.56 | 0.78 | 0.78 | 12.5 | 1.56 | 3.13 |
| Example 5-4 | 3.13 | 12.5 | 3.13 | 0.78 | 0.39 | 3.13 | 1.56 | 3.13 |
| Example 5-5 | 1.56 | 25 | 1.56 | 3.13 | ≦0.2 | 0.78 | 6.25 | 0.78 | 0.78 |
| Example 6 | 0.2 | 1.56 | 0.39 | 0.78 | ≦0.05 | 0.39 | 25 | 1.56 | 3.13 |
| Example 7-1 | ≦0.05 | 1.56 | 0.2 | 0.39 | >0.05 | 0.2 | 6.25 | 0.39 | 0.78 |
| Example 7-2 | ≦0.05 | 0.78 | 0.39 | 1.56 | ≦0.05 | 0.78 | 12.5 | 0.78 | 1.56 |
| Example 7-3 | 0.1 | 1.56 | 0.2 | 0.78 | ≦0.05 | 0.2 | 6.25 | 0.39 | 0.78 |
| Example 7-4 | 0.1 | 1.56 | 0.2 | 0.78 | ≦0.05 | 0.39 | 50 | 0.78 | 1.56 |

TABLE 4-continued

| | Gram-negative bacteria (mcg/ml) | | | | | | | | |
|---|---|---|---|---|---|---|---|---|---|
| Test compound | P. vulgaris IFO 3988 | P. vulgaris GN 4413 | P. mirabilis GN 4359 | P. morganii IFO 3168 | P. retgeri TN 338 | P. retgeri GN 4733 | E. cloacae IFO 12937 | C. freundii GN 99 | C. freundii GN 1706 |
| Example 8 | ≦0.05 | 0.39 | 0.2 | 0.2 | ≦0.05 | 0.39 | 0.78 | 0.2 | 0.39 |

We claim:

1. A compound of the formula:

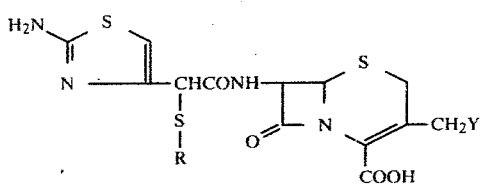

wherein R is lower alkyl or a group of the formula

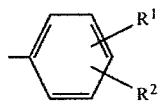

where R¹ and R² are the same or different and each is hydrogen, carboxyl or halogen; Y is $C_{2-4}$ alkylcarbonyloxy, acetoacetoxy or carbamoyloxy or a group of the formula —S—Het where Het is an unsubstituted or substituted pyridyl, N-oxopyridyl, pyrimidyl, pyridazinyl, N-oxopridazinyl, pyrazolyl, diazolyl, thiazolyl, thiadiazolyl, oxazolyl, oxadiazolyl, triazolyl or tetrazolyl wherein the substituent is $C_{1-4}$ alkyl, trifluoromethyl, $C_{1-4}$ alkoxy, halogen, hydroxyl, mercapto, amino, carboxyl, carbamoyl, or a group of the formula —(CH$_2$)$_n$—Q¹, —S—Q² or

where n is 1-3, Q¹ is hydroxyl, mercapto, amino, guanyl, morpholino, carboxyl, sulfo, carbamoyl, $C_{1-4}$ alkoxyl, $C_{1-4}$ alkylcarbamoyl, $C_{1-4}$ alkoxycarbonyl, $C_{1-4}$ alkylthio, $C_{1-4}$ alkylsulfonyl, $C_{2-4}$ acryloxy or morpholino-carbonyl, Q² is $C_{1-4}$ alkyl or —(CH$_2$)$_n$—Q¹, and Q³ and Q⁴ are $C_{1-4}$ alkyl, carboxyl, $C_{1-4}$ alkoxycarbonyl, $C_{1-4}$ acyl, carbamoyl, $C_{1-4}$ alkylcarbamoyl or —(CH$_2$)$_n$—Q¹ or a pharmaceutically acceptable salt thereof.

2. A compound as claimed in claim 1, wherein R is $C_{1-3}$ alkyl.

3. A compound as claimed in claim 2, wherein the $C_{1-3}$ alkyl is methyl.

4. A compound as claimed in claim 1, wherein R is a group of the formula

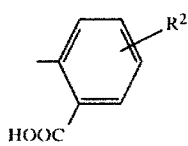

where R² is hydrogen or halogen.

5. A compound as claimed in claim 1, wherein R is a group of the formula

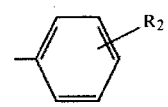

where R² is hydrogen or halogen.

6. A compound as claimed in claim 1, wherein the $C_{2-4}$ alkylcarbonyloxy is acetyloxy.

7. A compound as claimed in claim 1, wherein Y is a group of the formula:

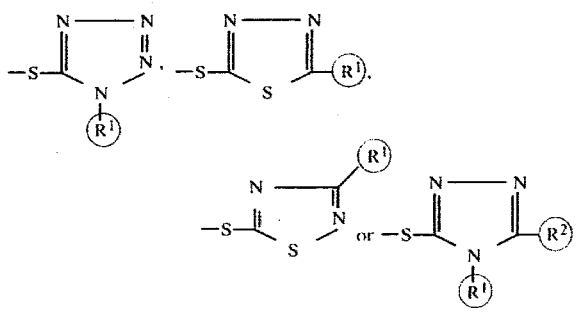

wherein R¹ is hydrogen, $C_{1-3}$ alkyl, hydroxy-$C_{1-3}$ alkyl, carboxy-$C_{1-3}$ alkyl or di-$C_{1-3}$ alkylamino-$C_{1-3}$ alkyl and R² is $C_{1-3}$ alkyl or hydroxy-$C_{1-3}$ alkyl.

8. A compound as claimed in claim 1, wherein Y is a group of the formula:

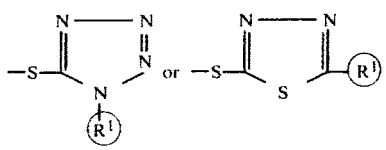

wherein R¹ is $C_{1-3}$ alkyl or di-$C_{1-3}$ alkyl-amino-$C_{1-3}$ alkyl.

9. A compound as claimed in claim 1, which is 7-[2-(2-aminothiazol-4-yl)-2-methylthioacetamido]-3-(1-methyl-1H-tetrazol-5-yl)thiomethyl-3-cephem-4-carboxylic acid.

10. A compound as claimed in claim 1, which is 7-[2-(2-aminothiazol-4-yl)-2-(2-carboxyphenylthio)acetamido]-3-(2-methyl-1,3,4-thiadiazol-5-yl)thiomethyl-3-cephem-4-carboxylic acid.

11. A compound as claimed in claim 1, which is 7-[2-(2-aminothiazol-4-yl)-2-(2-carboxyphenylthio)acetamido]cephalosporanic acid.

12. A compound as claimed in claim 1, which is 7-[2-(2-aminothiazol-4-yl)-2-(2-carboxyphenylthio)acetamido]-3-(1-methyl-1H-tetrazol-5-yl)thiomethyl-3-cephem-4-carboxylic acid.

13. A compound as claimed in claim 1, which is 7-[2-(2-aminothiazol-4-yl)-2-(2-carboxyphenylthio)acetamido]-3-(1,3,4-thiadiazol-2-yl)thiomethyl-3-cephem-4-carboxylic acid.

14. A compound as claimed in claim 1, which is 7-[2-(2-aminothiazol-4-yl)-2-(2-chlorophenylthio)acetamido]-3-(1-methyl-1H-tetrazol-5-yl)thiomethyl-3-cephem-4-carboxylic acid.

15. A compound as claimed in claim 1, which is 7-[2-(2-aminothiazol-4-yl)-2-(3-chlorophenylthio)acetamido]-3-(1-methyl-1H-tetrazol-5-yl)thiomethyl-3-cephem-4-carboxylic acid.

16. A compound as claimed in claim 1, which is 7-[2-(2-aminothiazol-4-yl)-2-(2-carboxy-5-chlorophenylthio)acetamido]-3-(1-methyl-1H-tetrazol-5-yl)thiomethyl-3-cephem-4-carboxylic acid.

17. A compound as claimed in claim 1, which is 7-[2-(2-aminothiazol-4-yl)-2-(2-carboxy-4-chlorophenylthio)acetamido]-3-(1-methyl-1H-tetrazol-5-yl)thiomethyl-3-cephem-4-carboxylic acid.

18. A compound as claimed in claim 1, which is 7-[2-(2-aminothiazol-4-yl)-2-(2-carboxy-6-chlorophenylthio)acetamido]-3-(1-methyl-1H-tetrazol-5-yl)thiomethyl-3-cephem-4-carboxylic acid.

19. A compound as claimed in claim 1, which is 7-[2-(2-aminothiazol-4-yl)-2-(2-carboxyphenylthio)acetamido]-3-[1-(2-dimethylaminoethyl)-1H-tetrazol-5-yl]thiomethyl-3-cephem-4-carboxylic acid.

* * * * *